US00PP08310P

United States Patent [19]

Vletter

[11] Patent Number: Plant 8,310

[45] Date of Patent: Jul. 20, 1993

[54] LILY PLANT NAMED WIDOR

[75] Inventor: Floris Vletter, Rijnsburg, Netherlands

[73] Assignee: Gebr. Vletter & J.A. den Haan, Rijnsurg, Netherlands

[21] Appl. No.: 796,534

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct lily plant named Widor, characterized by its very large flowers and floriferous habit; soft pink main flower color with the base of the tepals being yellow-green; long stems and pedicels, vigorous growth habit, and its contrasting orange pollen color.

1 Drawing Sheet

The present invention comprises a new and distinct cultivar of lily, botanically known as Lilium, commercially known as Lilium oriental hybrid, and hereinafter referred to by the cultivar name Widor. The parents were oriental varieties belonging to division VII(b) described in "Classification of Lily Cultivars into Divisions" published by Victoria Mathews, The Royal Botanic Gardens, Kew (1989).

The new cultivar is a product of a planned breeding program which had the primary objective of creating new lily cultivars having light pink main flower color, combined with a different color variegation, long stems, and other desired characteristics for cut flower production.

The new cultivar was originated from a hybridization made by the inventor in a controlled breeding program in Rijnsburg, The Netherlands in 1981. Both the male and female parents were unnamed seedlings.

The new cultivar was discovered and selected as one flowering plant within the progeny of the stated cross by the inventor in July 1981 in a controlled environment in Rijnsburg, The Netherlands.

The first act of asexual reproduction of the new cultivar was accomplished by the inventor when scales were taken from the initial selection in 1985 in a controlled environment in Rijnsburg, The Netherlands.

Horticultural examination of selected units has demonstrated that the combination of characteristics as herein disclosed for Widor are firmly fixed and are retained through successive generations of asexual reproduction.

The new cultivar has not been observed under all possible environmental conditions. The phenotype may vary significantly with variations in environment such as temperature, light intensity, and day length, without, however, any variation in genotype. The following observations, measurements and comparisons describe plants grown in Wageningen and Rijnsburg, The Netherlands under greenhouse conditions which approximate those generally used in commercial practice.

The following traits have been repeatedly observed and are determined to be basic characteristics of the new cultivar which in combination distinguish this lily as a new and distinct cultivar.

1. Large flowers and floriferous habit;
2. Soft pink flower color, with base of tepals being yellow-green in color;
3. Long stems and pedicels;

4. Contrasting orange pollen color;
5. Vigorous growth habit.

Of the many commercial cultivars known to the present inventor, the most similar in comparison to the new cultivar is Joy. In comparison to Joy, Widor has a lighter color, more spots on the tepals, and the flowers are oriented more horizontally. When flowering is forced under natural light, Widor produces an inflorescence approximately 4 days earlier than Stargazer, under the same growing conditions. Widor is fertile.

The accompanying photographic drawing shows typical flower characteristics of the new cultivar, with colors being as true as possible with illustrations of this type. In the photograph, there are several open flowers, and buds at various stages.

In the following description, color references are made to The Royal Horticultural Society (R.H.S.) Colour Chart. The color values were determined at Wageningen in 1988 and Rijnsburg in July 1991.

Origin: Seedling from Breeding Program.

Parentage:

*Seed parent.*—Unnamed seedling.

*Pollen parent.*—Unnamed seedling.

Classification:

*Botanical.*—Lilium.

*Commercial.*—Oriental hybrid.

THE PLANT

Form: A single stem carrying numerous pedicels alternately arranged.

Height: Medium to tall; 120 cm at time of opening of anthers of first flower.

Growth habit: Vigorous.

Stem: Color 144D; circular in transverse section; internodal length 1 cm and uniform; anthocyanin pigmentation present.

Foliage:

*Quantity.*—75–85 leaves depending on growing conditions.

*Size of leaf.*—Mature leaves are medium in length (18 cm), and medium to narrow in width (3.5 cm).

*Shape of leaves.*—Elliptical.

*Texture.*—Smooth with no glossiness; no pubescence.

*Color.*—Medium green 137B.

Bulbs:

*Size.*—Outlet 6–30 cm.

*Color.*—Cream.

Roots: Both stem and contractile present.

THE BUD

Form: Tapering (like a lancet).

Size: 11–13 cm prior to opening.

Opening: Unfolds normally.

Color: Yellowish with green midveins and a tinge of pink.

Tepals: Folded, three visible.

THE FLOWER

Blooming habit: Raceme.

Size: 22 cm in total diameter, depending on growing conditions.

Borne: Horizontal.

Shape: Generally in form of hexagonal star; bowl-shaped in cross-section.

Tepalage:

*Number of tepals.*—Six.

*Arrangement.*—Three inner and three outer each with moderate marginal undulation.

*Color.*—Upper surface: Light pink 52B-C, with base of petals and midveins toward base being yellow to yellow-green. Lower surface: Light pink 62C, with 2 mm strip of 62B at side edges.

*Spotting or marking.*—Red-purple spots elliptical on papillae; diameter 0.5–1.5 mm.

Nectaries and papillae: Present; strong.

Pedicel:

*Length.*—9 cm (of first flower).

*Color.*—Medium green with anthocyanin on upper part.

*Form.*—Strongly curved.

Texture: Papillose; strong.

Disease resistance: No disease problems noted to date.

Fragrance: Present; weak.

Lasting quality: Excellent.

REPRODUCTIVE ORGANS

Stamens, anthers:

*Arrangement.*—Anthers form a generally circular pattern.

*Length.*—Short to medium, 9 cm.

*Number.*—Six.

*Filaments.*—White/light yellow; top green.

Pollen color: Dark orange-brown.

Anther color: Red brown.

Pistils: Green style; top dark green; total length 11.5 cm.

Stigma: Triangular; green to grey-green stigma.

Ovaries: Triangular in shape other characteristics typical of oriental lily varieties.

I claim:

1. A new and distinct cultivar of lily plant named Widor, as illustrated and described.

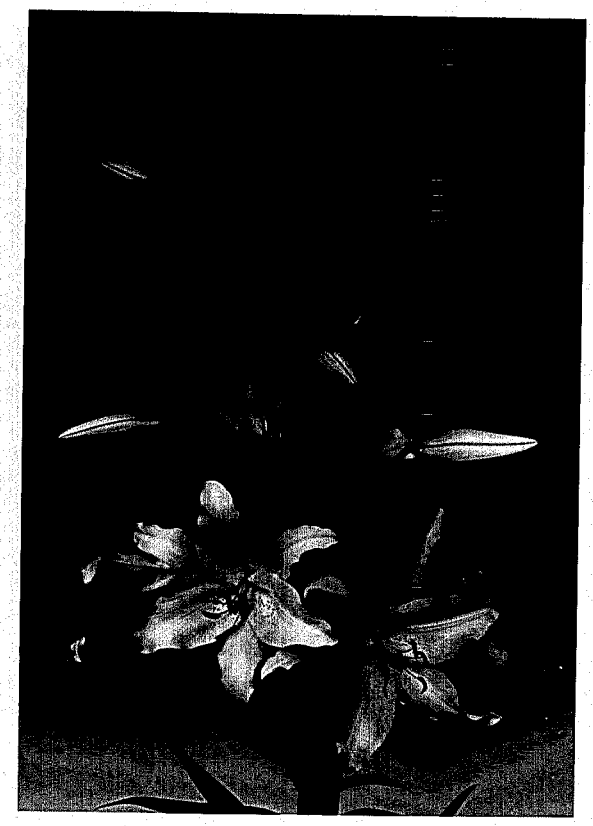

* * * * *